United States Patent [19]

Fusejima et al.

[11] Patent Number: 5,939,097
[45] Date of Patent: Aug. 17, 1999

[54] FOOD-LIKE MEDICINE

[75] Inventors: Yasutoyo Fusejima; Masayuki Ikeda; Toshiyuki Suzuki, all of Tokyo, Japan

[73] Assignee: Freund Industrial Co., Ltd., Tokyo, Japan

[21] Appl. No.: 08/619,531

[22] PCT Filed: Aug. 4, 1994

[86] PCT No.: PCT/JP94/01293

§ 371 Date: Mar. 21, 1996

§ 102(e) Date: Mar. 21, 1996

[87] PCT Pub. No.: WO96/03118

PCT Pub. Date: Feb. 8, 1996

[30] Foreign Application Priority Data

Jul. 21, 1994 [JP] Japan .................................. 6-169328

[51] Int. Cl.$^6$ ...................................................... A61K 9/48
[52] U.S. Cl. .......................... 424/451; 424/455; 514/944; 514/962
[58] Field of Search ..................................... 424/451, 439, 424/455, 456; 428/402, 402.2; 514/944, 962

[56] References Cited

U.S. PATENT DOCUMENTS

| | | | |
|---|---|---|---|
| 4,888,140 | 12/1989 | Schlameus et al. | 264/4.3 |
| 5,330,835 | 7/1994 | Kikuchi et al. | 428/402.22 |
| 5,385,737 | 1/1995 | Shigeno et al. | 424/451 |
| 5,387,093 | 2/1995 | Takei | 425/5 |
| 5,478,508 | 12/1995 | Suzuki et al. | 264/4 |
| 5,595,757 | 1/1997 | Kiefer et al. | 424/451 |
| 5,641,512 | 6/1997 | Cimiluca | 424/455 |
| 5,650,232 | 7/1997 | Glenn et al. | 428/402.2 |

Primary Examiner—Robert H. Harrison
Attorney, Agent, or Firm—Kane,Dalsimer,Sullivan, Kurucz, Levy, Eisele and Richard, LLP

[57] ABSTRACT

In a food-like medicine comprising a seamless capsule enclosing effective ingredients and at least one of a gel and a high viscous liquid, the seamless capsule has: a diameter (d) within a range of 0.5–5 mm, a relation of a membrane thickness (θ) of the seamless capsule to the diameter (d) being 0.01 d≦θ≦0.05 d, and a ratio (ρ) of a major axis to a minor axis of the seamless capsule not more than 1.3.

6 Claims, No Drawings

FOOD-LIKE MEDICINE

TECHNICAL FIELD

The present invention relates to an oral medicine, and more particularly to a food-like medicine having a novel orally administrable formulation.

BACKGROUND ART

Medicines have various formulations in accordance with their use, and as to oral medicines 16 kinds of formulations are described in the Pharmacopoeia of Japan, 9 of which are liquid formulations and the remaining 7 of which are solid formulations.

Although the liquid formulations among the oral medicines have the advantage of easy oral administration, their use is extremely limited because of the following reasons: medicines which are easily decomposed by moisture and humidity in the air cannot be applied to the liquid formulations; it is impossible to manufacture the liquid formulations considering drug delivery system (DDS) such as enteric formulations and sustained release dosage formulations; and off-tastes and off-flavors of the liquid formulations can be masked with great difficulty.

On the other hand, of 7 kinds of the solid formulations, there are basically 5 kinds which are swallowed in the solid state, namely, powder, granule, pills, tablets and capsules. Since these solid formulations in particular granule, tablets and capsules can overcome the disadvantages described in the case of the liquid formulations by varying design for the formulations, these formulations are widely utilized, recently.

Each of these solid formulations is usually swallowed with cold or hot water, but it is not always easy even for a healthy person to swallow a solid formulation smoothly. Powder or granule, for example, often adheres to the throat, and consequently the person feels an off-taste such as a bitter taste or sometimes coughs. The person also experiences difficulty in swallowing pills, tablets or capsules due to the degree of their size, the smoothness of their surface or the absorbability of water.

It is much more difficult for such persons as a child, a feeble person, a sickly person and an old person than for a healthy person to swallow these solid formulations. Even if these persons try with water, they often fail to swallow smoothly by coughing due to the high flowability of water, or swallow only water and leave the solid formulation in the mouth.

When a person cannot swallow the solid formulation in a usual way, the formulation may be administered by crushing it. However, if tablets are crushed, the masked off-tastes and off-flavors will be released in the mouth. Furthermore, in the case of the crushed enteric coated tablets or prolonged release dosage forms, the formulation not only cannot function but also can cause side-effects.

The primary users of medicines are not healthy persons but those, as mentioned above, who feel difficulty in swallowing the solid formulation. Considering a tendency to remarkable increase in population of aged persons, the problem of difficulty in administering the solid formulation cannot be ignored simply as a special case, but should be treated as a universal problem. That is to say, the community will request the research and development of the solid formulations wherein not only the functions such as the effects of medicines but also the easiness of the administration is pursued.

The present inventors have already proposed an easily administrable medicine comprising a seamless capsule enclosing effective ingredients and at least one of a gel and a high viscous liquid (Japanese Patent Laid-Open No. 5-139958). This invention has been quite useful in providing an easily administrable medicine having a novel orally administrable formulation for such a person as a child, a feeble person, a sickly person or an old person.

However, the seamless capsule used in this easily administrable medicine sometimes breaks when the seamless capsule is mixed with a gel or a high viscous liquid, while this mixture is stored, or when the mixture is administered, and leaks the enclosed effective ingredients, which leads to a problem: the person feels an off-taste such as a bitter taste.

Then, the present inventors have repeated studies in order to obtain the conditions whereunder the seamless capsule does not break which is used as a medicine having an orally administrable formulation, and consequently have accomplished the present invention.

It is an object of the present invention to provide a food-like medicine which can be easily swallowed by such a person as a child, a feeble person, a sickly person or an old person, and furthermore which can be safely administered without the possibility of leaking the effective ingredients.

DISCLOSURE OF THE INVENTION

The food-like medicine of the present invention comprises a seamless capsule enclosing effective ingredients and at least one of a gel and a high viscous liquid, a diameter (d) of the seamless capsule being within a range of 0.5–5 mm, a relation of a membrane thickness ($\theta$) of the seamless capsule to the diameter (d) being $0.01\ d \leq \theta \leq 0.05\ d$, and a ratio ($\rho$) of a major axis to a minor axis of the seamless capsule being not more than 1.3.

The diameter (d) of the seamless capsule is set to be the average value of the major and minor axes. When this value is less than 0.5 mm, a ratio of the membrane to the ingredients increases, whereby a large amount of the capsule is required in administering a predetermined amount of the medicine. Also, since the cost of manufacturing the seamless capsule is high, the manufactured medicine in this case is uneconomical. On the other hand, for the case of the diameter (d) greater than 5 mm, the manufactured medicine becomes swallowed with difficulty, and therefore is less practical. From the above point of view, the diameter (d) of the seamless capsule should be within a range of 0.5–5 mm, preferably of 0.8–4 mm, and more preferably of 1–3 mm.

For the case of the membrane thickness ($\theta$) of the seamless capsule less than 0.01 times the diameter (d) (for example, when the diameter is 1 mm, less than 10 $\mu$m of the thickness), the strength of the membrane weakens. Consequently, the membrane breaks when the seamless capsule mixed with a gel or a high viscous liquid swells, and leaks the ingredients before the medicine is administered.

To the contrary, if the membrane thickness ($\theta$) is greater than 0.05 times the diameter (d), a ratio of the membrane to the ingredients increases, whereby the same problem is caused as in the case of the diameter (d) less than 0.5 mm. Furthermore, after the medicine is administered, the thicker membrane takes longer time to dissolve inside the digestive organs, which is another problem. Here, the membrane thickness ($\theta$) of the seamless capsule is calculated by measuring the diameter (d) and the weight of the membrane only wherefrom the ingredients are removed.

As to the value of the ratio ($\rho$) of a major axis to a minor axis of the seamless capsule, if this value exceeds 1.3, the ununiformity of the membrane thickness becomes larger, and the locally thinner membrane causes the same problem as in the case of the membrane thickness (θ) of the seamless capsule less than 0.01 times the diameter (d). That is, a thinner part of the membrane breaks when the seamless capsule mixed with a gel or a high viscous liquid swells, and leaks the ingredients before the medicine is administered. Therefore, for the seamless capsule in particular having a diameter more than 2 mm, this ratio (ρ) should be not more than 1.2, preferably not more than 1.15.

In order to obtain the ratio (ρ) of a major axis to a minor axis of the seamless capsule, for example, a photograph of the seamless capsule which is placed on the horizontal plate is taken from a point above the capsule and is enlarged, and the maximum and minimum diameters of the seamless capsule in the enlarged photograph are measured.

As to the seamless capsule used in the medicine of the present invention, the outer layer of the capsule comprises gelatin or agar. A method of manufacturing the seamless capsule includes, for example, blowing out a droplet from a multiple nozzle into a hardening liquid, the droplet comprising the effective ingredients which should be enclosed and a coating agent with or without a solution such as a material for the middle layer, and hardening the droplet to be in a form of particle, whereby the size within a range about 0.5–5 mm, and more particular about 0.8–4 mm in diameter is easily made.

However, the seamless capsule manufactured by this method, under some condition, departs from the above-mentioned ranges on the relation of the membrane thickness to the diameter and on the ratio of a major axis to a minor axis. Therefore, in order effectively to manufacture the seamless capsule defined within these ranges, the seamless capsule should be manufactured so as to be in a satisfactory form of particle. This is done by employing, for example, the apparatus disclosed in Japanese Patent Laid-Open No. 5-138012 or No. 5-200274, or the method disclosed in No. 6-134292 whereto proper methods and conditions are further employed.

The seamless capsule having aforesaid characteristics has an advantage of easy swallowing with a gel or a high viscous liquid without the feel of a foreign body in the throat and with almost no masticating because of the affinity of the outer layer to a gel or a high viscous liquid and the smoothness of the surface due to the swelling when water is absorbed.

A gel used in the medicine of the present invention is defined as a gel in a broad sense, that is, colloidal or macromolecular solution in a solidified state having a structure wherein the colloidal particles or macromolecular solutes aggregate due to their interactions overcoming their independent movements ("Grand Chemical Dictionary" by Kyouritsu Shuppan).

More specifically, examples of the gel are the following edible gels: (1) agar gels such as agar, sweet jelly of beans (mizu-youkan), and the like; (2) pectin gels such as jam, marmalade, and the like; (3) mannan gels such as a paste made from the starch of the devil's tongue (konnyaku), noodles made from the starch of the devil's tongue (shirataki), and the like; (4) gelatin gels such as jelly, congealed food (nikogori), and the like; (5) protein gels such as custard pudding, thick custard soup (chawan-mushi), custard tofu (tamago-tofu), tofu, yogurt, and the like; (6) starch gels such as arrowroot starch, and the like; and (7) other gels such as carrageenan, xanthan gum, guar gum, tamarind, furcellaran, medlar (marmelo) extract, cardlan, and the like.

Examples of a high viscous liquid used in the medicine of the present invention are solutions such as arrowroot starch gruel, malt syrup, honey, and the like; and pasty emulsions or suspensions such as custard cream, shortening, chocolate paste, puree, ketchup, mayonnaise, and the like.

The gel or the high viscous liquid used in the medicine of the present invention needs to be at least edible, the texture, taste and smell of which are suitable for eating, and is processed as an easily administrable food-like product with almost no masticating.

Aforesaid examples of the gel or the high viscous liquid can be used individually, or can be mixed in a proper ratio for use. Furthermore, as other ingredients, adjuvant effective ingredients can be added such as a protective agent for digestive organs, an agent for nutrition supply, a digestive enzyme, and the like.

The medicine of the present invention is prepared by mixing the seamless capsule with the gel or the high viscous liquid either in advance or when the medicine is administered. In the case of mixing when administered, for example, liquid such as water or milk is added to powder or granular materials or moldings so as to prepare the desired gel or high viscous liquid, which in particular is useful for their storage and carriage.

According to the medicine of the present invention, the following desired effects are obtained: the seamless capsule enclosing effective ingredients is well covered with the gel or the high viscous liquid, which are never separated in the mouth; the lower flowability of the gel or the high viscous liquid than of water provides a person swallowing the medicine with no coughing; and due to the smoothness of its surface, the medicine as a solid formulation can be easily swallowed without masticating. Particularly, when the gel or the high viscous liquid is food, the medicine can be eaten as a dessert or a subsidiary food without a feeling of administering a medicine, and consequently such persons as a child, a feeble person, a sickly person and an old person enjoy the quite easy administration of the medicine.

Also, according to the medicine of the present invention, the further desired effect is obtained: the seamless capsule is now completely prevented from breaking when the seamless capsule is mixed with the gel or the high viscous liquid, while this mixture is stored, or when the mixture is administered, and from leaking the enclosed effective ingredients, thereby the person can safely administer the medicine without feeling an off-taste such as a bitter taste.

BEST MODE FOR CARRYING OUT THE INVENTION

Table 1 shows the properties of 8 samples (Examples 1–8) prepared by mixing the seamless capsule with the gel or the high viscous liquid. As comparative examples, 6 samples (Comparative Examples 1–6) and 4 samples (Comparative Examples 7–10) are prepared, the properties of which are shown in Table 2 and in Table 3, respectively.

The seamless capsules used in the samples shown in Tables 1–3 are supposed to enclose a 10% solution of 20 mg of effective ingredients, the numbers of which are as follows: 2 capsules for 5.2 mm in diameter, 4 capsules for 4 mm, 10 capsules for 3 mm, 33 capsules for 2 mm, about 150 capsules for 1.2 mm, and about 300 capsules for 1 mm.

Furthermore, as model ingredients enclosed in these seamless capsules, such immaterial ingredients are used as rapeseed oil, soybean oil, vitamin E, sucrose syrup, and the like since ingredients are not an important feature of the present invention. These ingredients, of course, can be substituted with effective ingredients in practice without departing from the scope of the invention.

TABLE 1

| | Classification | | | | | | Function | | |
|---|---|---|---|---|---|---|---|---|---|
| | Seamless Capsule | | | | | | Function | | |
| No. | d (mm) | ρ | θ (mm) | Material | Ingredient | Gel or High Viscous Liquid | Number of Breakages | Oral Administrability | Remarks |
| Example | | | | | | | | | |
| 1 | 0.8 | 1.18 | 0.012 | gelatin | rapeseed oil | jelly | 0 | ⊙ | Some are weak membranes |
| 2 | 1.0 | 1.10 | 0.040 | gelatin | rapeseed oil | custard pudding | 0 | ⊙ | |
| 3 | 1.0 | 1.08 | 0.015 | gelatin | rapeseed oil | chocolate paste | 0 | ⊙ | |
| 4 | 1.2 | 1.13 | 0.025 | agar | 65% sucrose syrup | arrowroot starch gruel | 0 | ⊙ | |
| 5 | 2.0 | 1.12 | 0.060 | gelatin | vitamin E | chocolate paste | 0 | ⊙ | |
| 6 | 3.0 | 1.12 | 0.040 | gelatin | vitamin E | custard pudding | 0 | ⊙ | |
| 7 | 4.0 | 1.10 | 0.080 | agar | soybean oil | jelly | 0 | ○ | |
| 8 | 3.0 | 1.25 | 0.040 | gelatin | vitamin E | custard pudding | 1 | ⊙ | |

TABLE 2

| | Classification | | | | | | Function | | |
|---|---|---|---|---|---|---|---|---|---|
| | Seamless Capsule | | | | | | Function | | |
| No. | d (mm) | ρ | θ (mm) | Material | Ingredient | Gel or High Viscous Liquid | Number of Breakages | Oral Administrability | Remarks |
| Comparative Example | | | | | | | | | |
| 1 | 1.0 | 1.42 | 0.040 | gelatin | rapeseed oil | custard pudding | 7 | ⊙ | Leakage |
| 2 | 1.0 | 1.16 | 0.008 | gelatin | rapeseed oil | custard pudding | 9 | ⊙ | Leakage |
| 3 | 2.0 | 1.08 | 0.015 | gelatin | vitamin E | chocolate paste | 15 | ⊙ | Leakage |
| 4 | 3.0 | 1.10 | 0.025 | gelatin | vitamin E | custard pudding | 12 | ⊙ | Leakage |
| 5 | 4.0 | 1.31 | 0.080 | agar | soybean oil | jelly | 5 | ○ | Leakage |
| 6 | 5.2 | 1.13 | 0.080 | gelatin | soybean oil | custard pudding | 0 | x | |

Note
(1). ρ: Photographs taken of 20 seamless capsules are enlarged, a ratio of a major axis to a minor axis of the seamless capsule in each photograph is measured, and the largest of these ratios is selected for the value.
(2). Number of Breakages: 20 seamless capsules added to 50 ml of a gel or a high viscous liquid are strongly stirred with a spoon in order to count the breakages.
(3). Separation: 20 seamless capsules added to 50 ml of a gel or a high viscous liquid are slightly mixed with a spoon, and are observed 1 hour after mixing.
(4). Oral Administrability: These samples are administered orally by 6 old persons who have difficulty in swallowing tablets in order to judge the oral administrability.
Judgment: ⊙ satisfactory, ○ almost satisfactory, x unusable

TABLE 3

| | Classification | | | | |
|---|---|---|---|---|---|
| No. | Formulation Solid Formulation | Gel or High Viscous Liquid | Size of Solid Formulation (mm) | Oral Administrability | Remarks |
| Comparative Example | | | | | |
| 7 | granule | — | about 1 | Δ | 2 persons feel slight difficulty in swallowing<br>4 persons feel an off-taste<br>1 person cannot swallow |
| 8 | tablet | — | 4 | x | All of 6 persons cannot swallow |
| 9 | hard capsule No. 5 | — | 5 × 11 | x | 1 person feel difficulty in swallowing<br>5 persons cannot swallow |
| 10 | powder | — | less than 0.5 | Δ | All of 6 persons feel uncomfortable<br>1 of them throws up |

Judgment: Δ no good, x unusable

Industrial Application

According to the food-like medicine of the present invention, since the solid formulation can be easily swallowed without masticating, not only a healthy person but also such persons as a child, a feeble person, a sickly person and an old person enjoy the quite easy oral administration of a medicine.

Furthermore, according to the food-like medicine of the present invention, the seamless capsule is completely prevented from breaking and leaking the enclosed effective ingredients, thereby the person can safely administer the medicine without feeling an off-taste such as a bitter taste.

We claim:

1. An orally ingestible delivery system comprising:
a component selected from the group consisting a gel, a highly viscous liquid, and mixtures thereof, in admixture with a seamless capsule, said capsule having a major axis, a minor axis, a diameter (d) and a membrane thickness ($\theta$), said seamless capsule enclosing effective ingredients, wherein the diameter (d) is between 0.5 and 5 mm and $0.01d \leq \theta \leq 0.05d$, and the ratio ($\rho$) of said major axis to said minor axis of the seamless capsule is not more than 1.3.

2. A orally ingestible delivery system according to claim 1 wherein the diameter (d) of the seamless capsule is between 0.8 to 4 mm.

3. A orally ingestible delivery system according to claim 1 wherein the diameter (d) of the seamless capsule is between 1 to 3 mm.

4. A orally ingestible delivery system according to claim 1 wherein $0.012d \leq \theta \leq 0.045d$.

5. A orally ingestible delivery system according to claim 1 wherein the ratio ($\rho$) of the major axis to the minor axis of the seamless capsule is not more than 1.2.

6. A orally ingestible delivery system according to claim 1 wherein the ratio ($\rho$) of the major axis to the minor axis of the seamless capsule is not more than 1.15.

* * * * *